United States Patent [19]

Throne

[11] Patent Number: 5,404,880
[45] Date of Patent: Apr. 11, 1995

[54] SCATTER DIAGRAM ANALYSIS SYSTEM AND METHOD FOR DISCRIMINATING VENTRICULAR TACHYARRHYTHMIAS

[75] Inventor: Robert D. Throne, Lincoln, Nebr.
[73] Assignee: Board of Regents of University of Nebraska, Lincoln, Nebr.
[21] Appl. No.: 131,648
[22] Filed: Oct. 5, 1993
[51] Int. Cl.[6] .............................................. A61B 5/04
[52] U.S. Cl. ..................................... 128/705; 128/706
[58] Field of Search ................ 128/696, 705, 706, 702
[56] References Cited

U.S. PATENT DOCUMENTS 4,422,459 12/1983 Simson .
5,000,189 3/1991 Throne et al. .
5,211,177 5/1993 Chesney et al. .

OTHER PUBLICATIONS

DiCarlo, Lorenzo A., et al., "Differentiation of Ventricular Tachycardia from Ventricular Fibrillation Using Intraventricular Electrogram Morphology", Sep. 1992.
Throne, Robert D., "Detecting Ventricular Fibrillation Using Efficient Techniques for Computing a Normalized Autocorrelation", Comput. Biol. Med., vol. 23, No. 4, pp. 317–325, 1993.
Throne, Robert D., et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, Jun. 1991, pp. 561–570.
Thakor, Nitish V., et al., "Ventricular Tachycardia and Fibrillation Detection by a Sequential Hypothesis Testing Algorithm", IEEE Transactions on Biomedical Engineering, vol. 37, No. 9, Sep. 1990, pp. 837–843.
Camm, A. John, et al., "Tachycardia Recognition by Implantable Electronic Devices", PACE, vol. 10, Sep.–Oct. 1987, pp. 1175–1277.
Davies, D. Wyn. et al., "Detection of Pathological Tachycardia by Analysis of Electrogram Morphology", PACE, vol. 9, Mar.–Apr. 1986, pp. 200–208.
Langberg, Jonathan J., et al., "Identification of ventricular tachycardia with use of the morphology of the endocardial electrogram", Circulation, vol. 77, No. 6, Jun. 1988, pp. 1363–1369.
Ripley, Kenneth L., et al., "Evaluation of Techniques for Recognition of Ventricular Arrhythmias by Implanted Devices", IEEE Transactions on Biomedical Engineering, vol., 36, No. 6, Jun. 1989, pp. 618–624.
Throne, Robert D., et al., "The Bin Area Method: A Computationally Efficient Technique for Anslysis of Ventricular and Atrial Intracardiac Electrograms", PACE, vol. 13, Oct. 1990, pp. 1286–1297.
Ropella, Kristina M., et al., "The Coherence Spectrum: A Quantative Discriminator of Fibrillatory and Nonfibrillatory Cardiac Rhythms", Circulation, vol. 80, No. 1, Jul. 1989, pp. 112–119.
Ropella, Kristina M., et al., "Differentiation of Ventricular Tachyarrhythmias", Circulation, vol. 82, No. 6, Dec. 1990, pp. 2035–2043.
Ropella, Kristina M., et al., "Effects of procainamide on intra-arterial electrograms during atrial fibrillation: implication for detection algorithms", Circulation, vol. 77, No. 5, May 1988, pp. 1047–1054.
S. Chen et al., "Ventricular fibrillation detection by a regression test on the autocorrelation function," Medical & Biol. Eng. & Comput., 1987, 25, 241–249.
D. Lin et al., "Identification of Ventricular Tachycardia Using Intracavitary Ventricular Electrograms: Analysis of Time and Frequency Domain Patterns," PACE, vol. 11, 1592–1606, Nov. 1988, Part I.

Primary Examiner—William E. Kamm
Assistant Examiner—Scott M. Getzow
Attorney, Agent, or Firm—Merchant, Gould, Smith, Edell, Welter & Schmidt

[57] ABSTRACT

A computationally efficient two channel scatter diagram analysis algorithm for distinguishing monomorphic ventricular tachycardia (VT) from polymorphic ventricular tachycardia and ventricular fibrillation (VF). Scatter diagram analysis plots the amplitude from one channel (morphology) versus the amplitude from another channel (rate) on a graph with a fifteen-by-fifteen grid. A fraction or percentage of the 225 grid blocks occupied by at least one sample point is then determined. Monomorphic VT traces nearly the same path in space and occupies a smaller percentage of the graph than a non-regular rhythm such as polymorphic VT or VF.

43 Claims, 10 Drawing Sheets

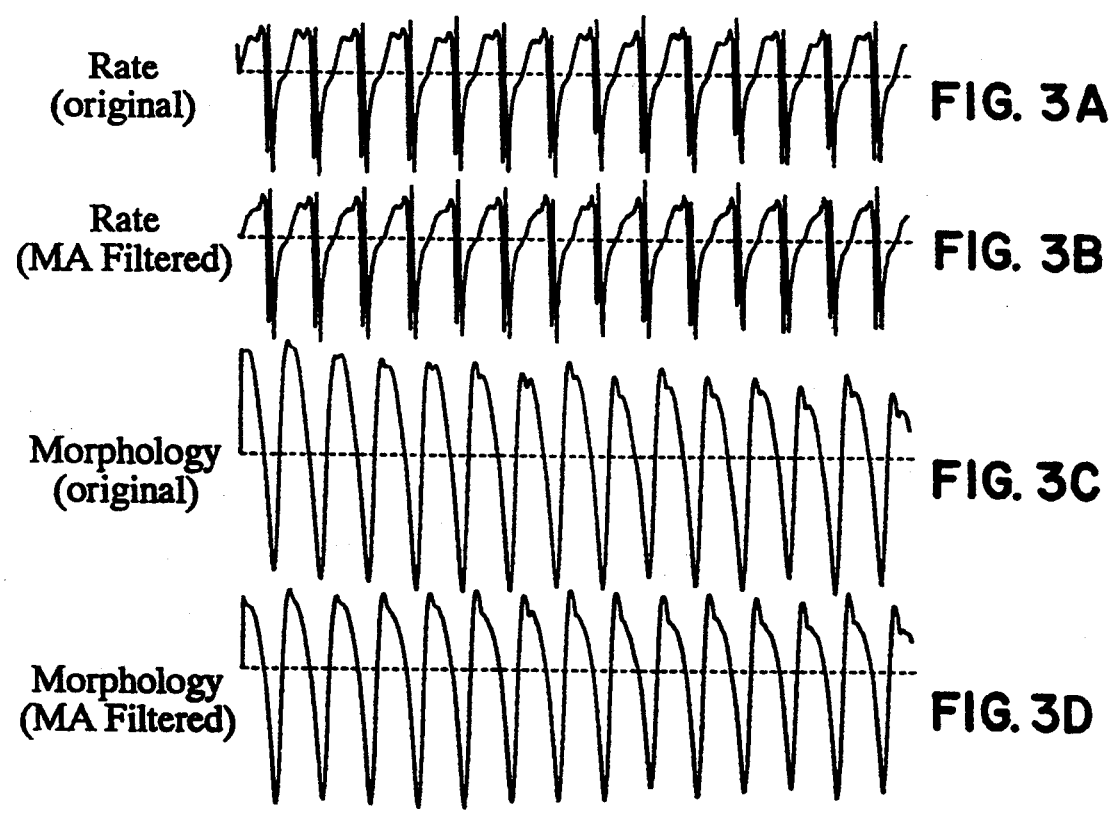
FIG. 3A Rate (original)
FIG. 3B Rate (MA Filtered)
FIG. 3C Morphology (original)
FIG. 3D Morphology (MA Filtered)

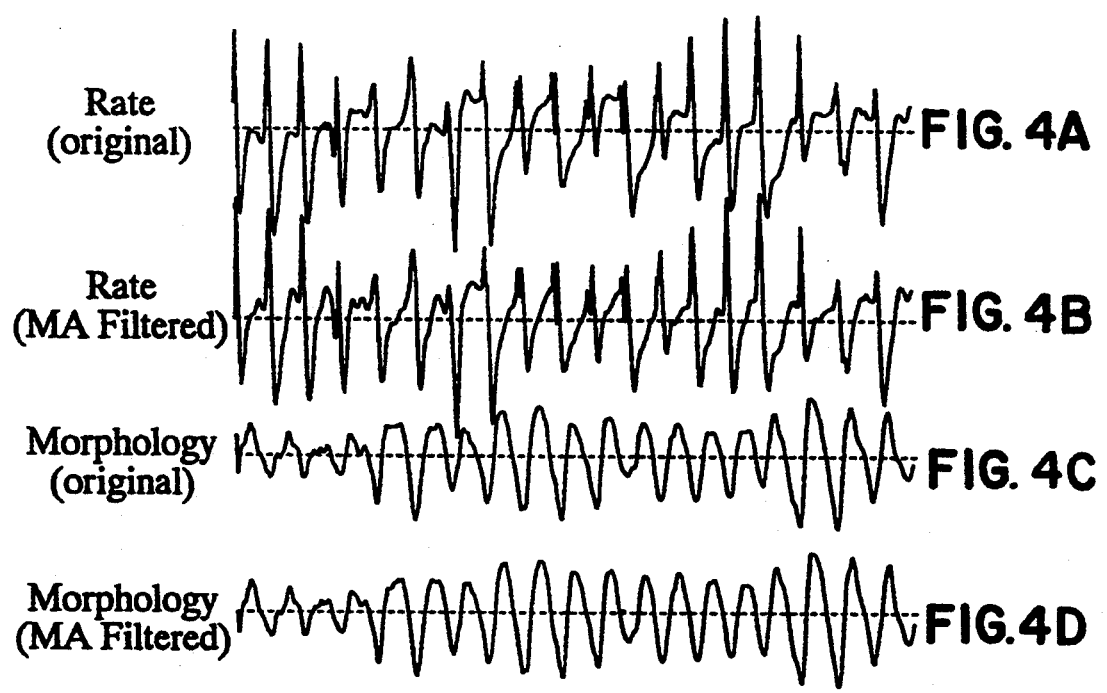

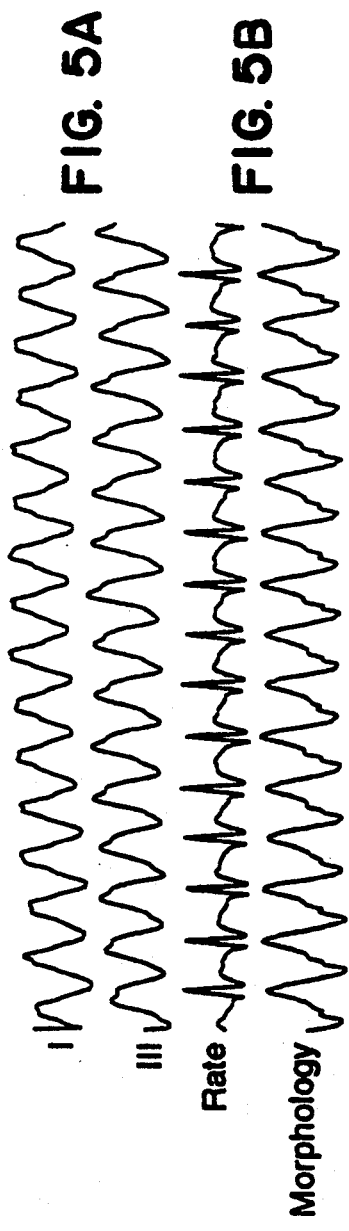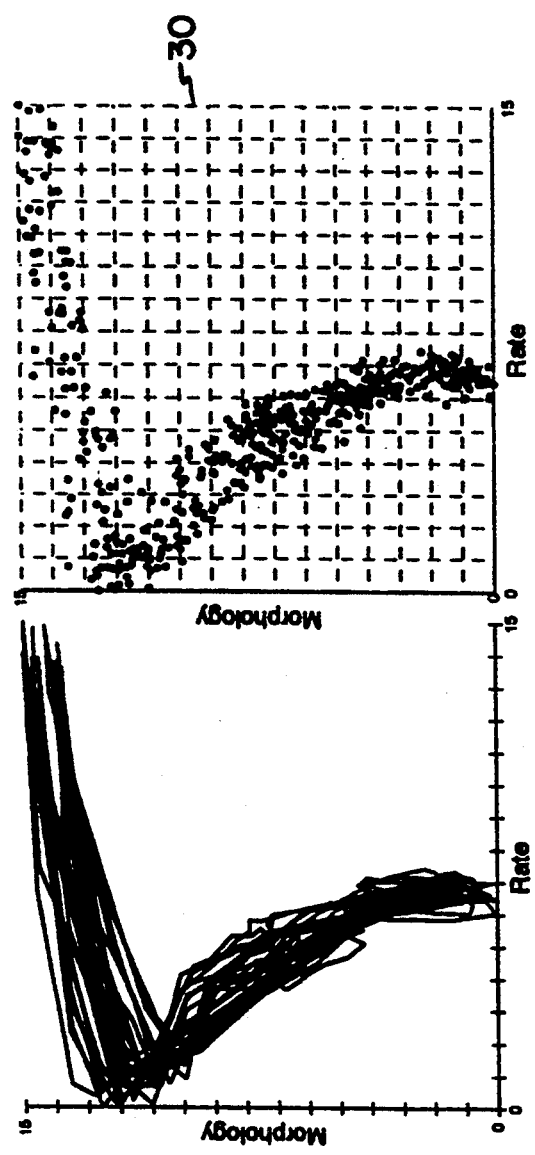

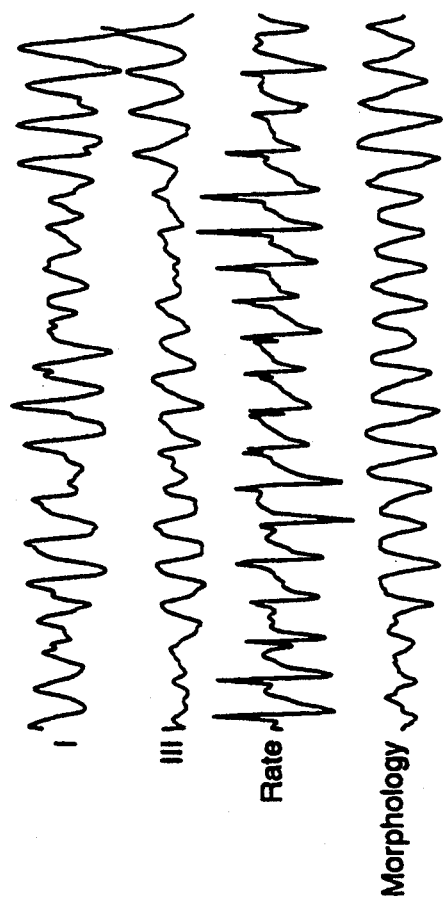
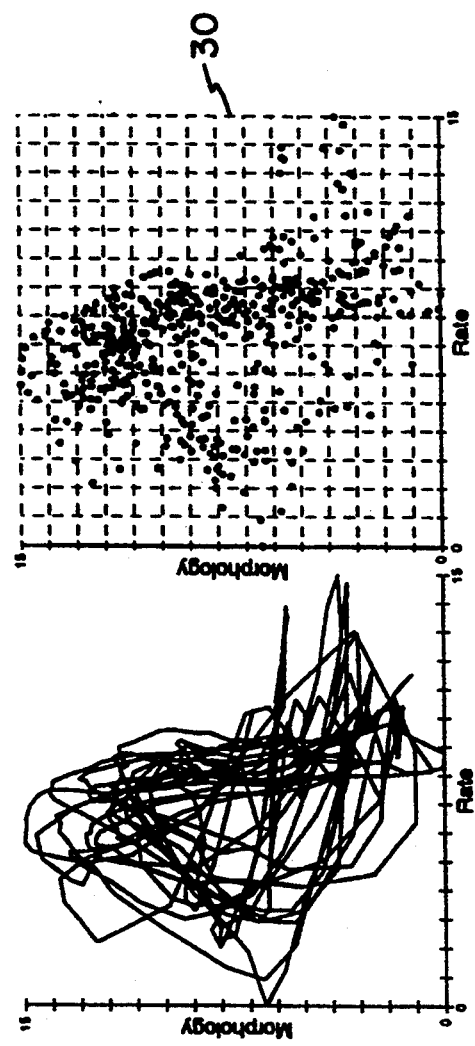
FIG. 6A
FIG. 6B
FIG. 6C
FIG. 6D

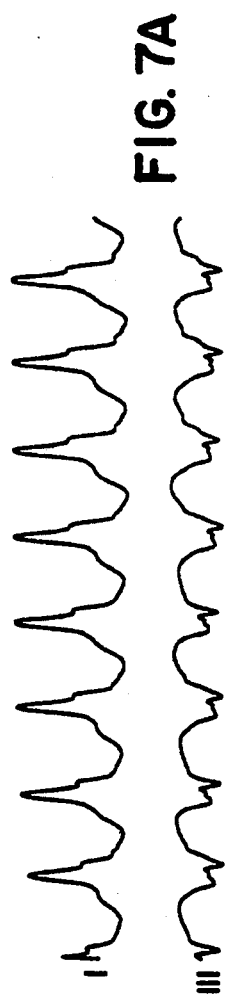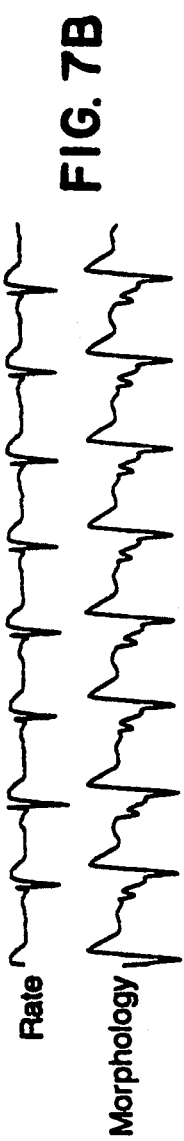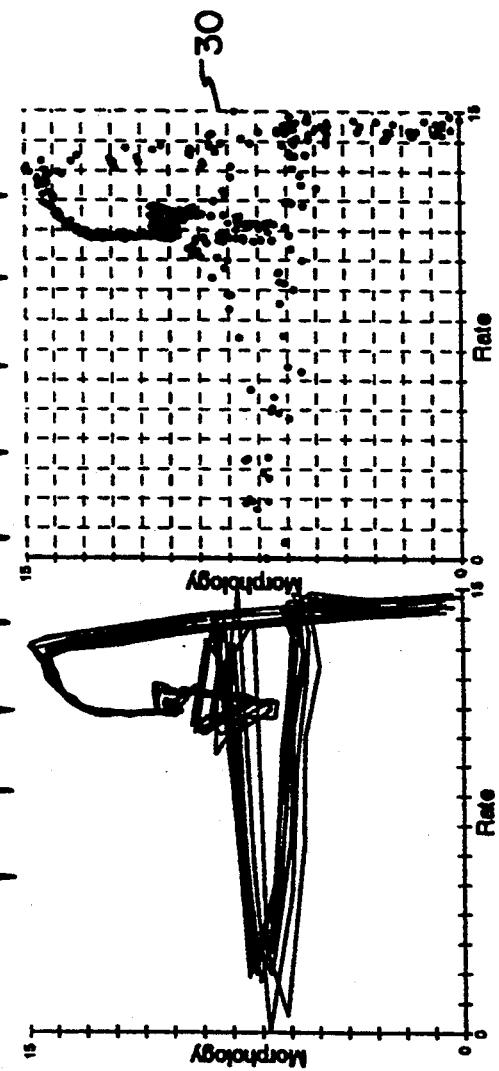
FIG. 7A
FIG. 7B
FIG. 7C
FIG. 7D

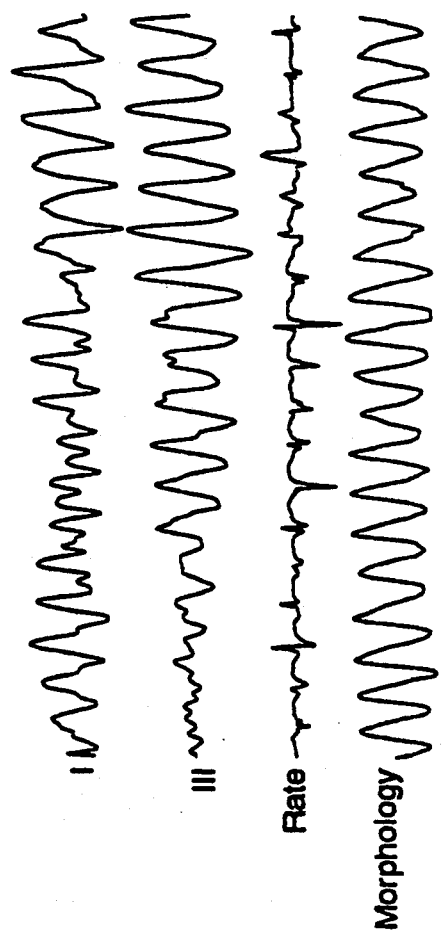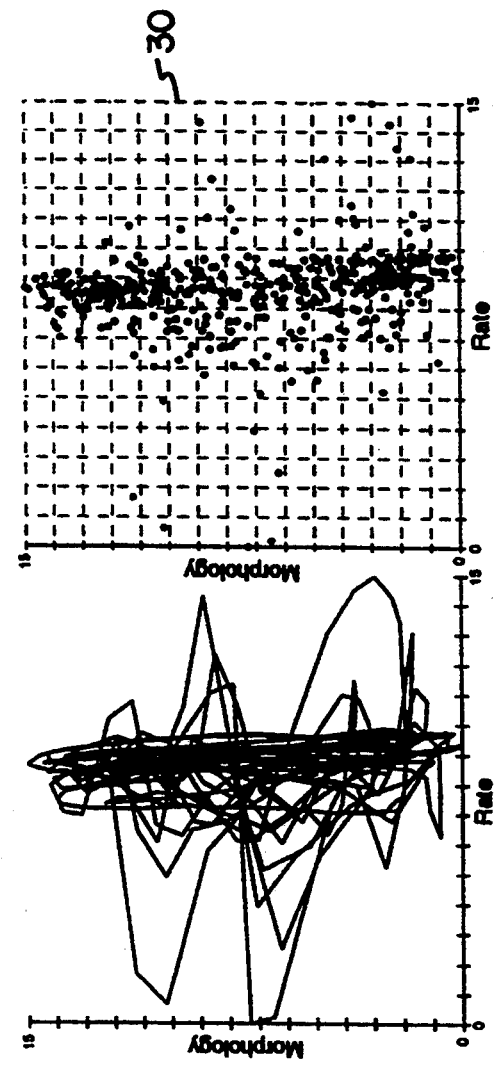

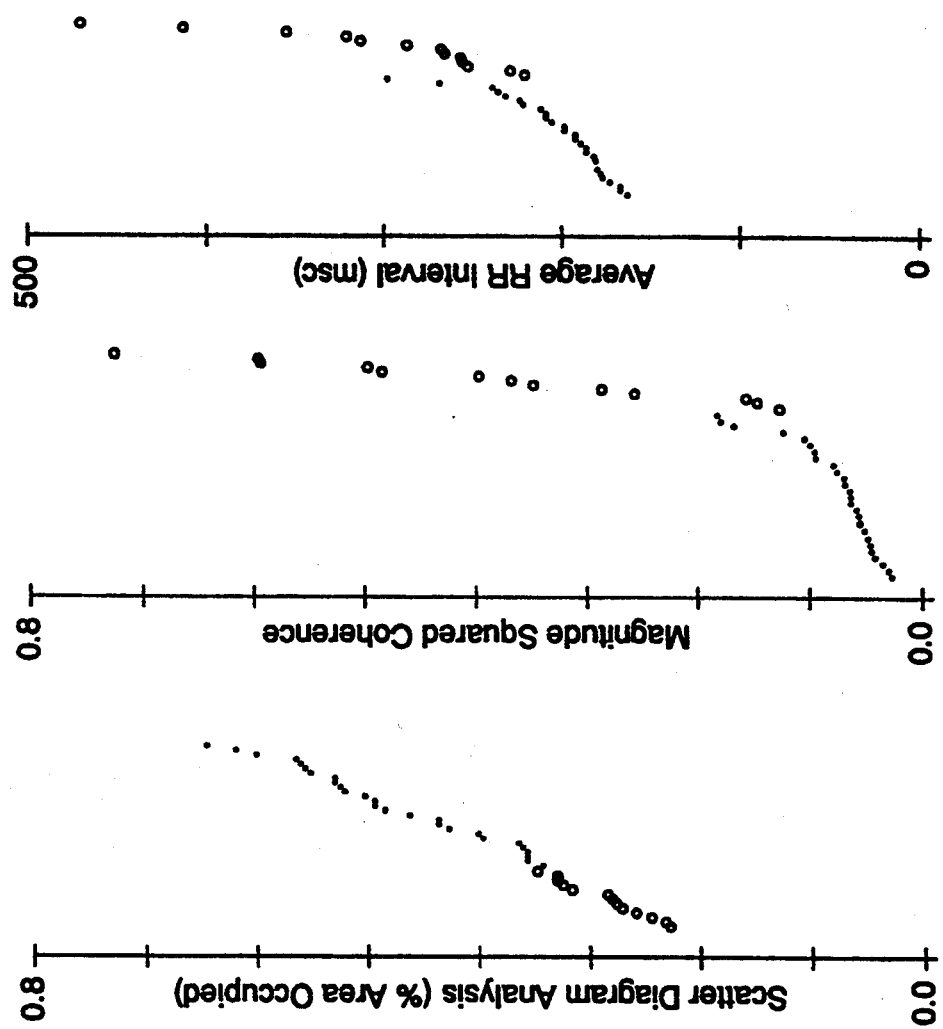

SCATTER DIAGRAM ANALYSIS SYSTEM AND METHOD FOR DISCRIMINATING VENTRICULAR TACHYARRHYTHMIAS

FIELD OF THE INVENTION

The present invention is a method and apparatus for analyzing electrocardiographic signals in order to discriminate ventricular tachyarrhythmias.

BACKGROUND OF THE INVENTION

With the introduction of new implantable cardioverters/defibrillators with tiered therapy, it is becoming possible to employ specific therapies for specific arrhythmias. Recently techniques based on computer analysis of the morphology changes in electrograms have been proposed for use in conjunction with rate-based algorithms for more accurate detection of ventricular tachyarrhythmias. These techniques include, for example, magnitude squared coherence.

Many of these techniques, however, are computationally very complex. A need thus exists for a computationally simple method of discriminating monomorphic ventricular tachycardia from polymorphic ventricular tachycardia and ventricular fibrillation.

SUMMARY OF THE INVENTION

This invention is a method, and system which executes the method, of discriminating ventricular tachyarrhythmias. The method analyzes two channels recording electrocardiographic signals from a patient's heart, such as morphology and corresponding rate measurements of the patient. The morphology and rate measurements are first sampled and digitized. A series of data points is then generated, which represent a graph of the data, the graph having a first dimension representing morphology and a second dimension representing rate. Finally, ventricular tachyarrhythmias of the patient are discriminated by determining a value representing a distribution of the data points on the graph.

BRIEF DESCRIPTION OF THE DRAWINGS

FIGS. 3A-3D are graphs showing original and filtered morphology and rate signals for a first patient.

FIGS. 4A-4D are graphs showing original and filtered morphology and rate signals for a second patient.

FIGS. 5A-5D are graphs showing scatter diagram analysis for a first patient in monomorphic ventricular tachycardia.

FIGS. 6A-6D are graphs showing scatter diagram analysis for a first patient in polymorphic ventricular tachycardia.

FIGS. 7A-7D are graphs showing scatter diagram analysis for a second patient in monomorphic ventricular tachycardia.

FIGS. 8A-8D are graphs showing scatter diagram analysis for a second patient in polymorphic ventricular tachycardia.

FIG. 10A is a graph showing the results of scatter diagram analysis for twenty-seven patients.

FIG. 10B is a graph showing the results of magnitude squared coherence for twenty-seven patients.

FIG. 10C is a graph showing an average rate of the twenty-seven patients analyzed in FIGS. 10A and 10B.

DETAILED DESCRIPTION OF THE PREFERRED EMBODIMENT

Figure 1:
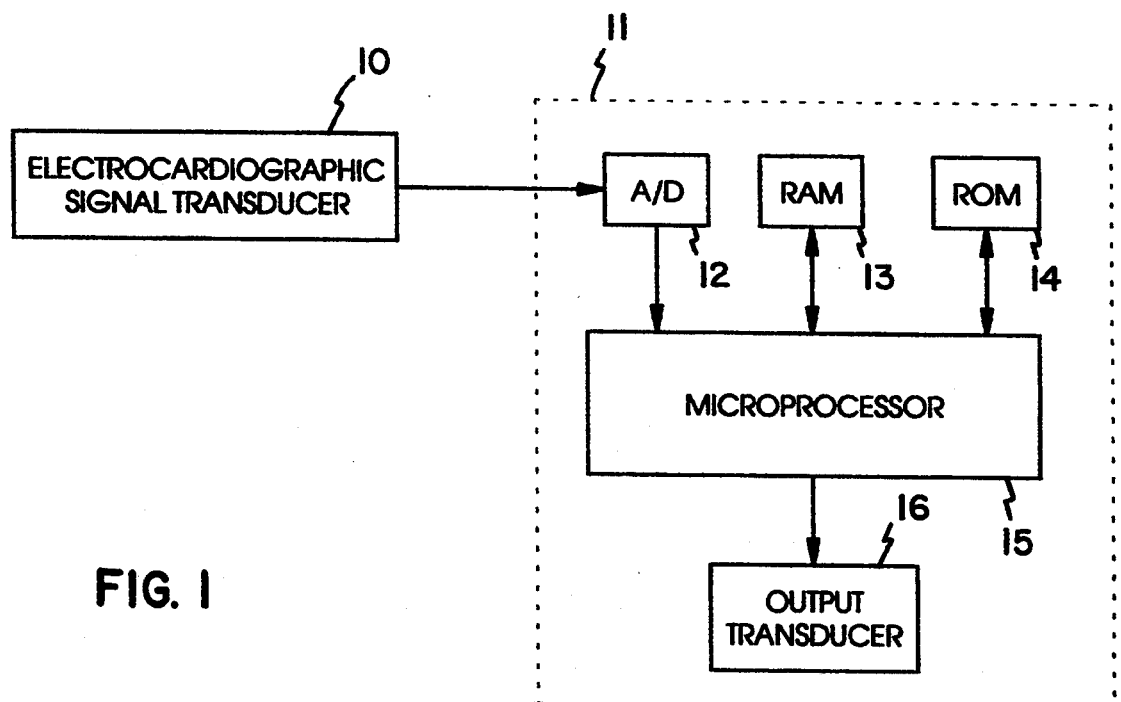
FIG. 1 is a block diagram of a system for performing scatter diagram analysis.

In the following detailed description of the preferred embodiment, reference is made to the accompanying drawings which form a part hereof and in which is shown by way of illustration a specific embodiment in which the invention may be practiced. This embodiment is described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

Scatter Diagram Analysis Method

With the increasing flexibility allowed by implantable cardioverter/defibrillators with tiered therapy, it is important to match the therapy with the arrhythmia. Scatter diagram analysis is a new computationally efficient two channel algorithm for distinguishing monomorphic ventricular tachycardia (VT) from polymorphic ventricular tachycardia and ventricular fibrillation (VF). Scatter diagram analysis preferably receives two channels recording electrocardiographic signals and plots the amplitude from one channel versus the amplitude from another channel on a graph, or alternatively computes a representation of such a graph. In the example shown, the two channels comprise a bipolar lead on the heart (referred to as a "rate" signal) and patches placed across the heart (referred to as a "morphology" signal). Scatter diagram analysis can operate on data received from any two channels recording electro-cardiographic signals from the heart. For example, instead of using patches for a "morphology" signal, scatter diagram analysis may use a "morphology" signal received from a coil in the right ventricle of a patient's heart.

Scatter diagram analysis then determines a distribution of the signals on the graph or, alternatively, a representation of a distribution. A signal distribution is typically determined by overlaying, for example, a fifteen-by-fifteen grid on the graph and computing the fraction (percentage) of the 225 grid blocks occupied by at least one sample point.

Scatter diagram analysis has revealed that monomorphic VT traces nearly a same path in space and occupies a smaller percentage of the graph than a non-regular rhythm such as polymorphic VT or VF. Scatter diagram analysis was tested on twenty-seven patients undergoing intraoperative implantable cardioverter/defibrillator testing. Passages of 4.096 seconds were obtained from both rate (bipolar epicardial) and morphology (patch) leads and digitized at 125 Hz. Scatter diagram analysis distinguished thirteen episodes of monomorphic VT ($28.6 \pm 4.0\%$) from twenty episodes of polymorphic VT or VF ($48.0 \pm 8.2\%$) with $p < 0.0005$. There was overlap in only one monomorphic VT episode and one polymorphic VT or VF episode.

Scatter diagram analysis is a computationally simple algorithm based on morphology changes during monomorphic VT and polymorphic VT and VF. In particular, scatter diagram analysis measures temporal changes between electrograms measured at two sites. Scatter diagram analysis was compared with average rate, magnitude squared coherence, and amplitude distribution analysis for its ability to differentiate monomorphic VT from polymorphic VT/VF.

FIG. 1 is a block diagram of a system for performing scatter diagram analysis. System 11 is interfaced to an electrocardiographic signal transducer 10, such as epicardial bipolar lead and defibrillating patches. An analog-to-digital converter 12 receives electrocardiographic signals, such as morphology and rate, and converts the signals into corresponding digital signals. A microprocessor 15 receives the digital morphology and rate signals and executes embedded software stored in ROM 14 in order to perform scatter diagram analysis on the signals. Microprocessor 15 is also typically coupled to a RAM 13 for storing data. After performing scatter diagram analysis on the signals, microprocessor 15 may output a signal to output transducer 16 in order to provide an indication of a patient's ventricular tachyarrhythmia or to transmit a control signal to another device such as a pacemaker.

In order to test scatter diagram analysis algorithm, data was collected as follows. This is an example of one method of data collection for scatter diagram analysis; other methods may be used for test data collection. Electrograms from both epicardial bipolar (approximately 1 cm spacing) lead and defibrillating patches were recorded on an instrumentation cassette tape recorder (TEAC R-71) from the output of an isolating amplifier and filtered at 1-500 Hz during initial defibrillator implantation, lead testing, or pulse generator replacement of an implantable cardioverter/defibrillator, such as the type manufactured by Cardiac Pacemakers, Inc. (CPI). Passages were initially digitized at 1000 Hz, then lowpass filtered (62.5 Hz) and decimated (every eighth sample point used) for an effective sampling rate of 125 Hz. This is one example of a method of data collection for scatter diagram analysis; other methods may be used to supply data. Passages of 512 pairs of sample points (4.096 seconds) were analyzed. Recordings were obtained from twenty-seven patients. There were thirteen episodes of monomorphic VT and twenty-seven episodes of polymorphic VT or ventricular fibrillation.

Figure 2:
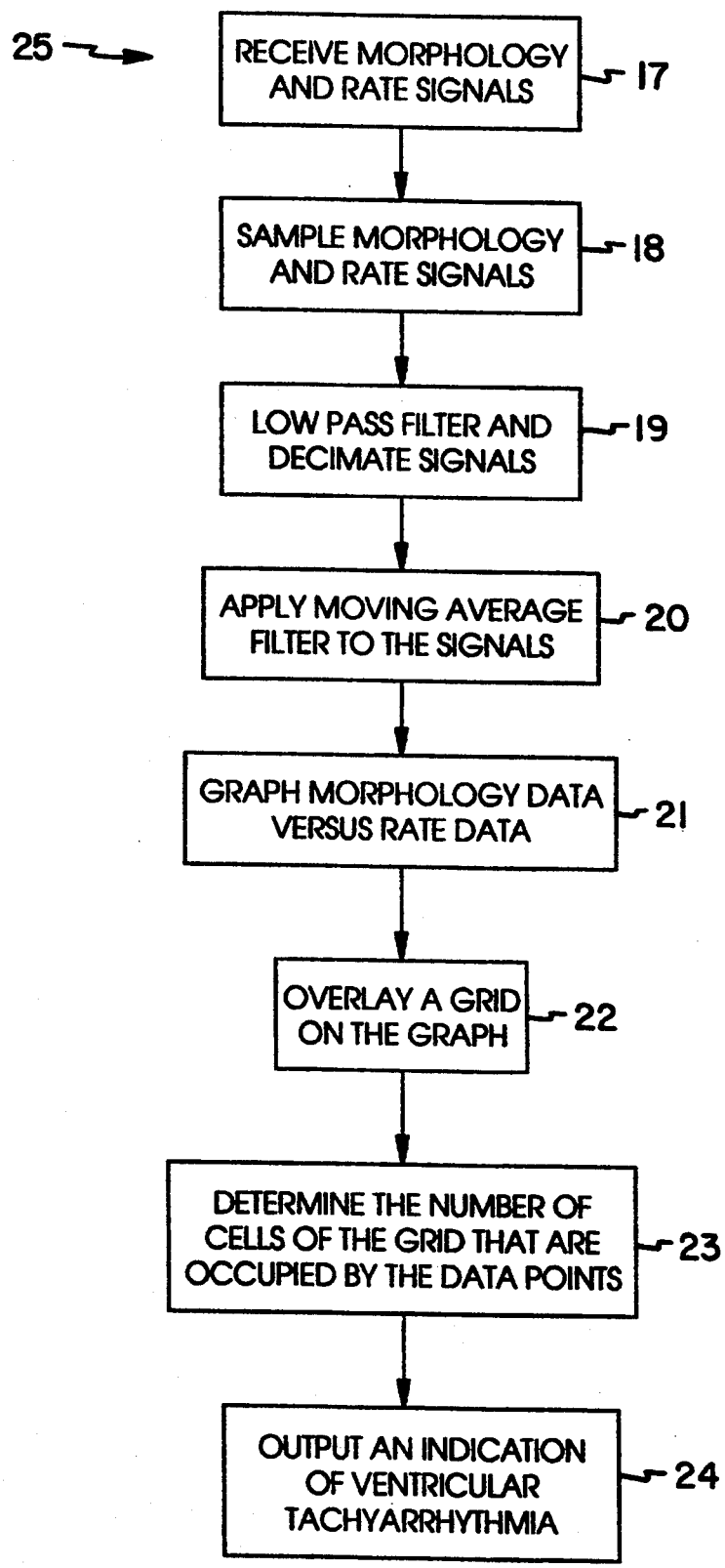
FIG. 2 is a flow chart of a method of discriminating ventricular tachyarrhythmias using scatter diagram analysis.

FIG. 2 is a flow chart of a scatter diagram analysis algorithm 25 executed by system 11. System 11 first receives morphology and rate signals at step 17. Microprocessor 15 samples the signals (step 18) and then lowpass filters and decimates the signals (step 19). A moving average filter is then typically applied to each of the two signals to be analyzed (step 20). This filter removes baseline fluctuations due to respiration by subtracting the local average from each sample point. The local average for any sample point was determined, in the example shown, by averaging thirty points centered at the sample point (sixteen points before, the current point, and fifteen points after).

System 11 next plots the amplitude of the morphology channel versus the amplitude of the rate channel (step 21). In the example shown, system 11 uses a two-dimensional graph with morphology plotted on the "y" axis and rate plotted on the "x" axis. Alternatively, morphology may be plotted on the "x" axis and rate plotted on the "y" axis. Furthermore, system 11 need not generate a physical graph of the signals; it may also generate data points which represent such a graph. At each sample point (i.e., at each time) there is a pair of x-y values to plot.

System 11 then determines a distribution of the signals on the graph. If the graph is not physically generated, system 11 may alternatively determine a representation of signal distribution. A distribution is preferably determined as follows. A grid is overlaid on a plot of the morphology channel amplitude versus the rate channel amplitude (step 22). The grid is typically divided into a plurality of cells. In the example shown, the grid has fifteen-by-fifteen dimensions and thus includes 225 cells. System 11 may use a grid having different dimensions or use different shaped cells for dividing the graph, as long as the graph is divided into a sufficient number of cells for determining a distribution of data points on the graph.

The number of these cells occupied with at least one sample point is then determined and the percentage of the cells (or grid) occupied is computed (step 23). Based on the percentage of cells occupied by data points, system 11 may output an indication of the tested patient's ventricular tachyarrhythmia (step 24).

System 11 typically does not generate a physical graph or grid in calculating a signal distribution. In the example shown, graphs and grids are used for conceptual purposes to illustrate scatter diagram analysis. Scatter diagram analysis algorithm 25 typically uses an algorithm for analyzing data points in order to determine a representation of a signal distribution of the data points. Table 1 illustrates an example of a first signal distribution algorithm in pseudo-code. Table 2 illustrates an example of a second signal distribution algorithm in pseudo-code. The second signal distribution algorithm assumes sixteen levels of signal amplitude within a known range.

TABLE 1

COMPUTE:
    minimum and maximum values for each channel;
    x = (maximum of x − minimum of x) / (number of cells);
    y = (maximum of y − minimum of y) / (number of cells);
DETERMINE the (x,y) boundaries of each cell;
INITIALIZE cell occupied counters to zero,
    i.e. cell(i,j) = 0 for the (i,j)th cell;
FOR each (x,y) pair of data points:
    IF (x,y) is in cell(i,j), THEN
        INCREMENT cell(i,j) counter;
COUNT the number of cell(i,j) counters NOT = 0
    to determine number of cells occupied
EXIT

TABLE 2

SET memory to all zeros;
FOR each (x,y) pair:
    LET 4 bits used for x-values representation
        be the first 4 bits of an 8-bit address;
    LET 4 bits used for y-values representation
        be the second 4 bits of an 8-bit address;
    WRITE a non-zero number at the specified 8-bit address;
COUNT the number of memory locations NOT = zero
    to determine the number of cells occupied
EXIT Monomorphic VT generally has a regular morphology from one depolarization to the next, and also has a regular relationship between channels. Hence, monomorphic VT typically traces the same path in a scatter diagram and occupies few of the cells. Polymorphic VT and VF will generally not have a regular morphology in at least one of the two channels, and there will not be a consistent relationship between the two channels. Hence, polymorphic VT and VF typically occupies a higher percentage of a scatter diagram grid cells. Polymorphic VT and VF were grouped together in the example shown. Scatter diagram analysis algorithm 25 was initially tested on data from one patient (not included in the results) to determine an appropriate grid size.

In addition to scatter diagram analysis, the electrograms in the example shown were analyzed using four previously validated algorithms: average rate, amplitude distribution analysis on both the rate and morphology channels, and magnitude squared coherence. In the example shown, algorithm 25 and the validation algorithms examined were all applied while the patients were in the supine position.

To determine the average rate, the signal was first differentiated. Then a threshold is set equal to 10% of the third largest value of this difference signal (positive or negative) and each crossing of this threshold by the absolute value of the differenced signal is counted. To prevent multiple counting during a single excursion a blanking (refractory) period is set to 150 milliseconds. The amplitude distribution analysis algorithm applied was similar to that described in the following reference, with the exception that the data was first differentiated rather than high pass filtered at 30 Hz. See Ropella K. M., Sahakian A. V., Baerman J. M., et. al.: Effects of procainamide on intra-atrial electrograms during atrial fibrillation: implication for detection algorithms, Circulation 1988; 77: 1047–1054.

Amplitude distribution analysis provides a measure of the "density" or the amount of time the signals spends at "baseline". The magnitude squared coherence algorithm was based on that described in the following references, utilizing thirty-one overlapping segments and thirty-two point FFTs. See Ropella K. M., Sahakian A. V., Baerman J. M., et. al.: The coherence spectrum: A quantitative discriminator of fibrillatory and nonfibrillatory cardiac rhythms, Circulation 1989; 80: 112–119; and Ropella K. M., Sahakian A. V., Baerman J. M., et. al.: Differentiation of ventricular tachyarrhythmias, Circulation 1990; 82: 2035–2043.

Results of Scatter Diagram Analysis

The following are the results of performing scatter diagram analysis 25 on the group of test patients described above. The results of applying the moving average filter on both monomorphic VT and VF is displayed in FIGS. 3A–3D and 4A–4D for passages of length 4.096 seconds. In FIG. 3A, the original rate channel is displayed, while the channel after the moving average filter is applied is displayed in FIG. 3B. The dotted line is only a reference for comparing the two signals. For this instance of monomorphic VT, the moving average filter changes the rate channel very little. FIGS. 3C and 3D show both the original and moving average filtered morphology channels. In this case the moving average filter does modify the signal more noticeably and makes the depolarizations look more regular. In addition, the downward trend at the end of the passage due to respiration has been removed.

FIGS. 4A–4D also display the results of moving average filtering on a 4.096 second passage of VF. Again, the original rate and filtered rate channels are displayed in FIGS. 4A and 4B, while the original and filtered morphology channels are displayed in FIGS. 4C and 4D. Again there is not much difference between the channels. The change in amplitude during respiration at the beginning of the passage has been removed by the moving average filter. There is very little change in the morphology channel using the moving average filter.

FIGS. 5A–5D and 6A–6D display the results of scatter diagram analysis for one patient while FIGS. 7A–7D and 8A–8D display the results for a second patient. In all of these figures, the top two rows represent surface leads I and III, while the third and fourth rows are the rate and morphology channels under analysis. The passage displayed is 4.096 seconds and the moving average filter has been applied to the rate and morphology channels.

FIG. 5C is a scatter diagram plotting the (x,y) pairs of points. For each morphology channel sample point (or y value) there is a corresponding rate channel sample point (or x value). These pairs of points have been connected to show the evolution of the signal over time. As FIG. 5C shows, the morphology and rate channels during this monomorphic VT trace more or less the same path in a scatter diagram. FIG. 5D is identical to FIG. 5C except the points are not connected. A fifteen-by-fifteen grid 30, for example, is overlaid on a scatter diagram shown in FIG. 5D, making up 225 cells. If any sample point lies within a cell, algorithm 25 preferably identifies the corresponding cell as occupied. For this passage, only a relatively small number of cells are occupied. The percentage of the cells occupied for this passage is 27.6.

FIGS. 6A–6D demonstrate scatter diagram analysis for the same patient in a polymorphic rhythm. Surface leads I and III are shown in FIG. 6A; the rate and morphology leads are shown in FIG. 6B. Again, this is a 4.096 second passage. As FIGS. 6A–6D indicate there is no consistent temporal relationship between the morphology and rate channels. A plot in FIG. 6C displays the results of plotting the morphology and rate sample pairs and following their evolution in time by connecting the pairs with lines. There appears to be no real order or organization to the pattern. A plot in FIG. 6D displays only the plotted points with, for example, a fifteen-by-fifteen grid 30 overlaid. Again, algorithm 25 determines a percentage of grid cells which contain at least one point; for this example the percentage of the area occupied is 48.4. This compares to the 27.6 percent area occupied by the same patient's monomorphic VT.

FIGS. 7A–7D display the results of scatter diagram analysis for a different patient in monomorphic VT. The rate and morphology channels, shown in FIGS. 7A and 7B, display a regular morphology. A plot in FIG. 7C indicates a consistent relationship between the channels. A scatter diagram in FIG. 7D indicates that the sample points occupy only 22.6 percent of the cells.

FIGS. 8A–8C presents the results of scatter diagram analysis for the same patient in a polymorphic rhythm. Here the rate channel displays a fairly irregular morphology while the morphology channel is fairly regular, as shown in FIGS. 8A and 8B. A plot in FIG. 8C indicates no consistent relationship between the two channels. A scatter diagram in FIG. 8D indicates the sample points occupy only 35.6 percent of the cells, compared to 22.6 percent of the cells for the same patient's monomorphic VT.

Figure 9B:
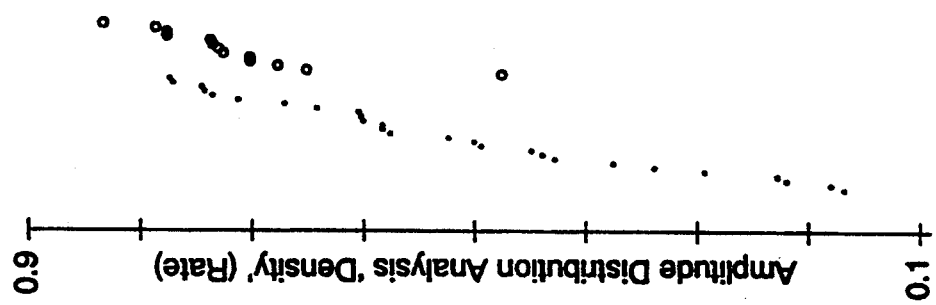
FIGS. 9A and 9B are graphs showing the results of amplitude distribution analysis for twenty-seven patients using rate and morphology signals.
Figure 9A:
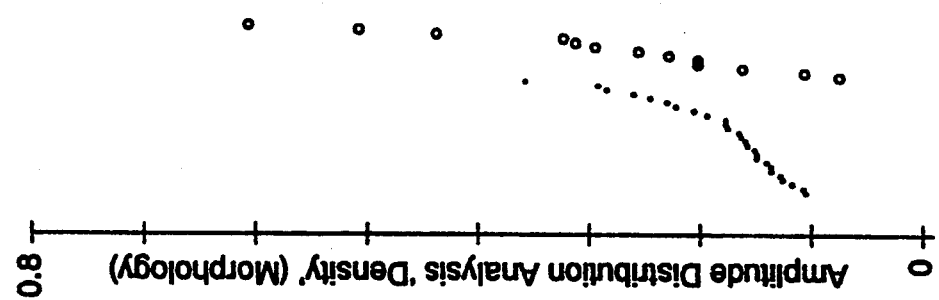

FIGS. 9A and 9B show the results for all twenty-seven patients described above for amplitude distribution analysis using both the bipolar (rate) and patch (morphology) leads. FIGS. 10A-10C show the results for all patients for scatter diagram analysis, magnitude squared coherence, and average rate. For each method of analysis, values for the monomorphic VT instances are displayed as open circles, while values for polymorphic VT/VF are shown as filled in circles.

The average "density" for amplitude distribution analysis using rate leads was 0.714±0.087 (mean±-standard deviation) for monomorphic VT and 0.517±0.188 for polymorphic VT/VF. There were nine instances of monomorphic VT below the highest density for polymorphic VT/VF. The average density for amplitude distribution analysis using the morphology leads was 0.284±0.155 and 0.181±0.062 for the monomorphic VT and polymorphic VT/VF episodes, respectively. Using the morphology leads and amplitude distribution analysis ten episodes of monomorphic VT had lower densities than the largest density of polymorphic VT/VF.

For scatter diagram analysis the average percentage of the cells occupied, in the example shown, during each passage of monomorphic VT was 28.6±4 percent, while polymorphic VT and VF occupied 48.0±8.2 percent. Using scatter diagram analysis monomorphic VT could be distinguished from polymorphic VT or VF with p<0.0005. The percent area occupied of one monomorphic VT overlapped with the percent area occupied of one polymorphic VT or VF. The average magnitude squared coherence during monomorphic VT was 0.382±0.189 while during polymorphic VT/VF it was 0.077±0.043. The magnitude squared coherence for three monomorphic VT episodes occurred below the highest magnitude squared coherence for polymorphic VT/VF. The average cycle length for monomorphic VT and polymorphic VT/VF was 299.7±73.6 and 202.1±31.5, respectively. There were eight episodes of monomorphic VT below the largest cycle length for polymorphic VT/VF.

As the summary graphs (FIGS. 9A-9B and FIGS. 10A-10C) indicate, only scatter diagram analysis and magnitude squared coherence were effective at discriminating monomorphic VT from polymorphic VT/VF. Using amplitude distribution analysis with the rate leads, there were nine monomorphic VT episodes overlapping seventeen polymorphic VT/VF episodes, while using the morphology leads there were ten monomorphic VT episodes overlapping twenty-seven polymorphic VT/VF episodes. Using average rate, there were eight episodes of monomorphic VT below the slowest polymorphic VT/VF. Using scatter diagram analysis there is overlap in only one instance of monomorphic VT with one instance of polymorphic VT/VF, while with magnitude squared coherence there is overlap in three instances of monomorphic VT with polymorphic VT/VF. All three independent observers identified the polymorphic VT/VF episode overlapping using scatter diagram analysis as VF, while two of the three polymorphic VT/VF episodes overlapping with magnitude squared coherence were identified as VF by all three observers. (The third overlapping episode using magnitude squared coherence was identified as polymorphic VT by all three observers.)

In this analysis magnitude squared coherence was considered to be the gold standard. However, magnitude squared coherence is very computationally demanding for use in currently available implantable cardioverter/defibrillators. While signal processing chips are available which can compute the magnitude squared coherence in real time, such chips require space in an implantable cardioverter/defibrillator and also draw substantial power.

Scatter diagram analysis performs similarly to magnitude squared coherence, but requires significantly fewer computations. The use of a moving average filter in scatter diagram analysis may initially appear to require a division for each sample point in computing the mean. However, since the computation may be performed using integer arithmetic, the division by thirty-two is simply implemented by a shifting operation. Similarly, scaling the electrograms to have a range of amplitudes from zero to fifteen initially appears to require a multiplication (or division) for each sample point. However, it is easier to determine the minimum and maximum electrogram amplitudes within the passage, and then determine the cell boundaries from these values. Hence there are only a total of twenty-eight multiplies required for all of the data analyzed. In addition, most currently available implantable cardioverter/defibrillators have automatic gain control to scale electrograms to a predetermined size. If the electrograms were digitized with fifteen levels the multiplications could be avoided entirely.

While the present invention has been described in connection with the preferred embodiment thereof, it will be understood that many modifications will be readily apparent to those skilled in the art, and this application is intended to cover any adaptations or variations thereof. For example, a different sized grid, or different cell shapes, may be used in determining signal distribution without departing from the scope of the invention. It is manifestly intended that this invention be limited only by the claims and equivalents thereof.

What is claimed is:

1. A method of discriminating ventricular tachyarrhythmias, comprising the steps of:
   (a) receiving data representing a first channel and a second channel both recording electrocardiographic signals from a patient's heart;
   (b) generating a series of data points, each of the data points having a first data element corresponding to the first channel and a second data element corresponding to the second channel; and
   (c) discriminating ventricular tachyarrhythmias of the patient by determining a value representing a distribution of the data points.

2. The method of claim 1 wherein step (c) comprises the steps of:
   (a) assigning memory addresses to a predetermined range of the data points; and
   (b) determining how many of the memory addresses correspond to at least one of the data points.

3. The method of claim 2 wherein step (c) further comprises the step of determining a percentage of the memory addresses that correspond to at least one of the data points.

4. The method of claim 3 wherein step (c) further comprises the step of determining if the percentage is greater than or less than a predetermined threshold value.

5. The method of claim 1 wherein step (c) comprises the step of discriminating monomorphic ventricular tachycardia from polymorphic ventricular tachycardia of the patient by comparing the value to a predetermined threshold value.

6. The method of claim 1 wherein step (a) comprises the steps of:
   (a) receiving a first electrocardiographic signal from the patient's heart and a corresponding second electrocardiographic signal from the patient's heart; and
   (b) sampling the first electrocardiographic signal and the second electrocardiographic signal in order to obtain the data.

7. The method of claim 1 wherein step (a) comprises the step of applying a moving average filter to the data.

8. The method of claim 1 wherein step (a) comprises the step of receiving data representing morphology and corresponding rate measurements of the patient's heart.

9. A method of discriminating ventricular tachyarrhythmias, comprising the steps of:
   (a) receiving data representing morphology and corresponding rate measurements of a patient's heart;
   (b) generating a series of data points, each of the data points having a first data element corresponding to the morphology measurements and a second data element corresponding to the rate measurements; and
   (c) discriminating ventricular tachyarrhythmias of the patient by determining a value representing a distribution of the data points.

10. The method of claim 9 wherein step (c) comprises the steps of:
    (a) assigning memory addresses to a predetermined range of the data points; and
    (b) determining how many of the memory addresses correspond to at least one of the data points.

11. The method of claim 10 wherein step (c) further comprises the step of determining a percentage of the memory addresses that correspond to at least one of the data points.

12. The method of claim 11 wherein step (c) further comprises the step of determining if the percentage is greater than or less than a predetermined threshold value.

13. The method of claim 9 wherein step (c) comprises the step of discriminating monomorphic ventricular tachycardia from polymorphic ventricular tachycardia of the patient by comparing the value to a predetermined threshold value.

14. The method of claim 9 wherein step (a) comprises the steps of:
    (a) receiving a morphology signal and a corresponding rate signal of the patient; and
    (b) sampling the morphology signal and the rate signal in order to obtain the data.

15. The method of claim 14 wherein the step of sampling further comprises the step of decimating the sampled morphology and rate signals.

16. The method of claim 9 wherein step (a) comprises the step of applying a moving average filter to the data.

17. A method of discriminating ventricular tachyarrhythmias, comprising the steps of:
    (a) receiving morphology data and corresponding rate data for a particular patient;
    (b) applying a moving average filter to the morphology data and the rate data;
    (c) plotting the morphology data and the rate data, using a plurality of data points, on a graph having a first dimension representing morphology and second dimension representing rate;
    (d) overlaying a grid, comprising a plurality of cells, on the graph of the morphology and rate data; and
    (e) discriminating ventricular tachyarrhythmias of the patient by determining a value related to how many of the cells are occupied by the data points.

18. The method of claim 17 wherein step (c) comprises the step of discriminating monomorphic ventricular tachycardia from polymorphic ventricular tachycardia of the patient by comparing the value to a predetermined threshold value.

19. The method of claim 17 wherein step (c) comprises the step of determining a percentage of the cells that are occupied by the data points.

20. The method of claim 19 wherein step (c) further comprises the step of determining if the percentage is greater than or less than a predetermined threshold value.

21. The method of claim 17 wherein step (a) comprises the steps of:
    (a) receiving a morphology signal and a corresponding rate signal of the patient; and
    (b) sampling the morphology signal and the rate signal in order to obtain the data.

22. The method of claim 17 wherein step (d) comprises the step of dividing the graph according to a grid of cells having predetermined dimensions.

23. A system for discriminating ventricular tachyarrhythmias, comprising:
    receive means for receiving data representing a first channel and a second channel both recording electrocardiographic signals from a patient's heart;
    means for generating a series of data points, each of the data points having a first data element corresponding to the first channel and a second data element corresponding to the second channel; and
    analysis means for discriminating ventricular tachyarrhythmias of the patient by determining a value representing a distribution of the data points.

24. The system of claim 23 wherein the analysis means comprises:
    means for assigning memory addresses to a predetermined range of the data points; and
    means for determining how many of the memory addresses correspond to at least one of the data points.

25. The system of claim 24 wherein the analysis means further comprises means for determining a percentage of the memory addresses that correspond to at least one of the data points.

26. The system of claim 25 wherein the analysis means further comprises means for determining if the percentage is greater than or less than a predetermined threshold value.

27. The system of claim 23 wherein the analysis means comprises means for discriminating monomorphic ventricular tachycardia from polymorphic ventricular tachycardia of the patient by comparing the value to a predetermined threshold value.

28. The system of claim 23 wherein the receive means comprises:
    means for receiving a first electrocardiographic signal from the patient's heart and a corresponding second electrocardiographic signal from the patient's heart; and means for sampling the first electrocardiographic signal and the second electrocardiographic signal in order to obtain the data.

29. The system of claim 23 wherein the receive means comprises means for applying a moving average filter to the data.

30. The system of claim 23 wherein the receive means comprises means for receiving data representing morphology and corresponding rate measurements of the patient's heart.

31. A system for discriminating ventricular tachyarrhythmias, comprising:
receive means for receiving electrocardiographic signals from a patient's heart, comprising:
means for receiving morphology signals; and
means for receiving rate signals;
sampling means for sampling the morphology signals and the rate signals in order to produce a set of morphology data and rate data;
means for generating a series of data points, each of the data points having a first data element corresponding to the morphology data and a second data element corresponding to the rate data; and
analysis means for discriminating ventricular tachyarrhythmias of the patient by determining a value representing a distribution of the data points.

32. The system of claim 31 wherein the analysis means comprises:
means for assigning memory addresses to a predetermined range of the morphology data and the rate data; and
means for determining how many of the memory addresses correspond to at least one of the data points.

33. The system of claim 32 wherein the analysis means comprises means for determining a percentage of the memory addresses that correspond to at least one of the data points.

34. The system of claim 33 wherein the analysis means further comprises means for determining if the percentage is greater than or less than a predetermined threshold value.

35. The system of claim 31 wherein the analysis means comprises means for discriminating monomorphic ventricular tachycardia from polymorphic ventricular tachycardia of the patient by comparing the value to a predetermined threshold value.

36. The system of claim 31 wherein the receive means comprises means for applying a moving average filter to the data.

37. The system of claim 31 wherein the sampling means comprises means for decimating the sampled morphology and rate signals.

38. A system for discriminating ventricular tachyarrhythmias, comprising:
receive means for receiving morphology data and corresponding rate data for a particular patient;
filter means for applying a moving average filter to the morphology data and the rate data;
graphing means for plotting the morphology data and the rate data, using a plurality of data points, on a graph having a first dimension representing morphology and second dimension representing rate;
grid means for overlaying a grid, comprising a plurality of cells, on the graph of the morphology data and the rate data; and
analysis means for discriminating ventricular tachyarrhythmias of the patient by determining a value related to how many of the cells are occupied by the data points.

39. The system of claim 38 wherein the analysis means comprises means for discriminating monomorphic ventricular tachycardia from polymorphic ventricular tachycardia of the patient by comparing the value to a predetermined threshold value.

40. The system of claim 38 wherein the analysis means comprises means for determining a percentage of the cells that are occupied by the data points.

41. The system of claim 40 wherein the analysis means further comprises means for determining if the percentage is greater than or less than a predetermined threshold value.

42. The system of claim 38 wherein the receive means comprises:
means for receiving a morphology signal and a corresponding rate signal of the patient; and
means for sampling the morphology signal and the rate signal in order to obtain the data.

43. The system of claim 42 wherein the sampling means comprises means for decimating the sampled morphology and rate signals.

* * * * *